United States Patent
Oshiro et al.

(10) Patent No.: US 10,294,347 B2
(45) Date of Patent: May 21, 2019

(54) PLASTICIZER FOR HALOGEN-BASED RESIN

(71) Applicant: KAO CORPORATION, Tokyo (JP)

(72) Inventors: Kojun Oshiro, Wakayama (JP); Masaaki Tsuchihashi, Wakayama (JP)

(73) Assignee: KAO CORPORATION, Tokyo (JP)

( * ) Notice: Subject to any disclaimer, the term of this patent is extended or adjusted under 35 U.S.C. 154(b) by 56 days.

(21) Appl. No.: 15/536,042

(22) PCT Filed: Nov. 11, 2015

(86) PCT No.: PCT/JP2015/081774
§ 371 (c)(1),
(2) Date: Jun. 14, 2017

(87) PCT Pub. No.: WO2016/098496
PCT Pub. Date: Jun. 23, 2016

(65) Prior Publication Data
US 2017/0349727 A1    Dec. 7, 2017

(30) Foreign Application Priority Data

Dec. 18, 2014 (JP) ................................. 2014-256433

(51) Int. Cl.
| | | |
|---|---|---|
| C08L 11/00 | (2006.01) | |
| C08K 5/12 | (2006.01) | |
| C08L 27/00 | (2006.01) | |
| C07D 307/68 | (2006.01) | |
| C08K 5/00 | (2006.01) | |

(52) U.S. Cl.
CPC ............... C08K 5/12 (2013.01); C08L 11/00 (2013.01); C08L 27/00 (2013.01); C07D 307/68 (2013.01); C08K 5/0016 (2013.01); C08K 2201/014 (2013.01)

(58) Field of Classification Search
USPC .................................................. 525/165, 169
See application file for complete search history.

(56) References Cited

U.S. PATENT DOCUMENTS

| | | | |
|---|---|---|---|
| 2012/0202725 | A1 | 8/2012 | Grass et al. |
| 2012/0220507 | A1 | 8/2012 | Grass et al. |
| 2013/0331491 | A1 | 12/2013 | Becker et al. |
| 2013/0338276 | A1 | 12/2013 | Becker et al. |
| 2014/0024754 | A1 | 1/2014 | Becker et al. |
| 2014/0128623 | A1 | 5/2014 | Janka et al. |
| 2014/0128624 | A1 | 5/2014 | Janka et al. |
| 2017/0121456 | A1* | 5/2017 | Bae ...................... C08G 63/916 |

FOREIGN PATENT DOCUMENTS

| | | |
|---|---|---|
| JP | 2001-207002 A | 7/2001 |
| JP | 2013-503120 A | 1/2013 |
| JP | 2013-503125 A | 1/2013 |
| JP | 2014-506618 A | 3/2014 |
| JP | 2014-507438 A | 3/2014 |
| JP | 2014-512342 A | 5/2014 |
| WO | WO 2013/184661 A1 | 12/2013 |
| WO | WO 2014/074482 A1 | 5/2014 |
| WO | WO 2014/074484 A1 | 5/2014 |
| WO | WO 2014/099438 A2 | 6/2014 |
| WO | WO 2014/193634 A1 | 12/2014 |
| WO | WO 2014/193635 A1 | 12/2014 |

OTHER PUBLICATIONS

International Search Report for PCT/JP2015/081774 (PCT/ISA/210) dated Feb. 16, 2016.
Sanderson et al., "Synthesis and Evaluation of Dialkyl Furan-2,5-Dicarboxylates as Plasticizers for PVC", Journal of Applied Polymer Science, vol. 53, (1994), pp. 1785-1793.
Yu et al., "Evaluating Effects of Biobased 2,5-Furandicarboxylate Esters as Plasticizers on the Thermal and Mechanical Properties of Poly(vinyl chloride)", J. Appl. Polym. Sci., 2014, 131(20), pp. 40938/1-40938/10.
Chinese First Office Action and Search Report (including partial English translation) issued in the corresponding Chinese Patent Application No. 201580066573.7 dated Nov. 27, 2018.

* cited by examiner

*Primary Examiner* — Terressa Boykin
(74) *Attorney, Agent, or Firm* — Birch, Stewart, Kolasch & Birch, LLP

(57) ABSTRACT

The present invention relates to [1] a plasticizer for a halogen-based resin including a condensate obtainable by an esterification reaction between a furan dicarboxylic acid compound and an aliphatic alcohol having 4 to 22 carbon atoms, in which the aliphatic alcohol includes a saturated aliphatic alcohol and an unsaturated aliphatic alcohol, and a content of the unsaturated aliphatic alcohol in the aliphatic alcohol is not more than 25% by mass; and [2] a halogen-based resin composition including the aforementioned plasticizer. The plasticizer has a plasticization performance for a halogen-based resin at a level identical to or higher than that of a phthalate-based plasticizer, and exhibits excellent effects of improving compatibility, heat resistance and cold resistance.

5 Claims, No Drawings

PLASTICIZER FOR HALOGEN-BASED RESIN

FIELD OF THE INVENTION

The present invention relates to a plasticizer for a halogen-based resin which contains a furan dicarboxylic acid diester, and a halogen-based resin composition containing the plasticizer.

BACKGROUND OF THE INVENTION

A vinyl chloride-based resin such as polyvinyl chloride (PVC) is an important resin used as a general-purpose polymer in various application fields. For example, the vinyl chloride-based resin is used in the form of hard PVC, soft PVC, etc., in the application fields such as pipes, building materials, packaging materials, agricultural materials, sheathing for electric cables, interior materials, wall paper materials, etc. For the purpose of mainly improving processability of the vinyl chloride-based resin and imparting good flexibility to a final product obtained from the vinyl chloride-based resin, a plasticizer is added to the resin.

As the plasticizer, phthalate-based plasticizers (such as dioctyl phthalate (DOP), diisononyl phthalate (DINP) and didecyl phthalate (DDP)) have been generally used conventionally. However, these phthalate-based plasticizers tend to have a risk of causing toxicity to environments. For this reason, in recent years, it has been required that the phthalate-based plasticizers are replaced with the other plasticizers that are capable of maintaining a good performance similar to that of the phthalate-based plasticizers.

As the non-phthalate-based plasticizers, there are known acetyl tributyl citrate (ATBC), di 2-ethylhexyl adipate (DOA), tri 2-ethylhexyl trimellitate (TOTM), etc. However, these non-phthalate-based plasticizers are deteriorated in their performance as compared to the phthalate-based plasticizers. For example, ATBC is deteriorated in heat resistance, DOA is deteriorated in compatibility with the vinyl chloride-based resin, and TOTM is deteriorated in plasticization efficiency.

PTL1 discloses a cyclohexane dicarboxylic acid ester such as bis(isononyl)cyclohexane-1,2-dicarboxylic acid ester (DINCH) which is used as a non-phthalate-based plasticizer for a vinyl chloride-based resin and is excellent in total valance of properties thereof, and also discloses di 2-ethylhexyl terephthalate (DOTP) as an alternate material.

PTL2 to PTL8 disclose esters of a furan dicarboxylic acid and an alcohol having 4 to 13 carbon atoms which are used as a plasticizer for a vinyl chloride-based resin.

CITATION LIST

Patent Literature

PTL1: JP 2001-207002A
PTL2: JP 2014-506618A
PTL3: JP 2014-507438A
PTL4: JP 2013-503120A
PTL5: JP 2013-503125A
PTL6: JP 2014-512342A
PTL7: US 2014/128623A
PTL8: US 2014/128624A

SUMMARY OF THE INVENTION

The present invention relates to a plasticizer for a halogen-based resin including a condensate obtainable by an esterification reaction between a furan dicarboxylic acid compound and an aliphatic alcohol (A) having not less than 4 and not more than 22 carbon atoms, in which the aliphatic alcohol (A) includes a saturated aliphatic alcohol (a1) and an unsaturated aliphatic alcohol (a2), and a content of the unsaturated aliphatic alcohol (a2) in the aliphatic alcohol (A) is not more than 25% by mass, and a halogen-based resin composition including the aforementioned plasticizer.

DETAILED DESCRIPTION OF THE INVENTION

DINCH and DOTP described in the aforementioned PTL1 have poor compatibility with a vinyl chloride-based resin, and therefore fail to exhibit satisfactory plasticization efficiency.

Also, the alcohols used in the esters described in the aforementioned PTL2 to PTL8 are substantially constituted of saturated alcohols only, and no studies on unsaturated alcohols have been made therein.

Furthermore, the plasticizers described in the aforementioned PTLs have such a problem that if it is intended to maintain plasticization performance of the plasticizers at a level identical to or higher than that of the phthalate-based plasticizers, they tend to suffer from deterioration in their properties such as compatibility, heat resistance and cold resistance.

The present invention relates to a plasticizer for a halogen-based resin which has a plasticization performance for a halogen-based resin at a level identical to or higher than that of a phthalate-based plasticizer, and exhibits excellent effects of improving compatibility, heat resistance and cold resistance, and a halogen-based resin composition including the plasticizer.

The present inventors have found that when a condensate obtainable by an esterification reaction between a furan dicarboxylic acid and an aliphatic alcohol having 4 to 22 carbon atoms and containing an unsaturated component is used as a plasticizer for a halogen-based resin, it is possible to solve the aforementioned conventional problems.

That is, the present invention relates to the following aspects [1] and [2]. [1] A plasticizer for a halogen-based resin including a condensate obtainable by an esterification reaction between a furan dicarboxylic acid compound and an aliphatic alcohol (A) having not less than 4 and not more than 22 carbon atoms, in which the aliphatic alcohol (A) includes a saturated aliphatic alcohol (a1) and an unsaturated aliphatic alcohol (a2), and a content of the unsaturated aliphatic alcohol (a2) in the aliphatic alcohol (A) is not more than 25% by mass. [2] A halogen-based resin composition including the plasticizer as defined in the above aspect [1].

In accordance with the present invention, it is possible to provide a plasticizer for a halogen-based resin which has a plasticization performance for a halogen-based resin at a level identical to or higher than that of a phthalate-based plasticizer, and exhibits excellent effects of improving compatibility, heat resistance and cold resistance, and a halogen-based resin composition including the plasticizer.

[Plasticizer for Halogen-Based Resin]

The plasticizer for a halogen-based resin according to the present invention (hereinafter also referred to merely as a "plasticizer") is characterized by being a condensate obtainable by an esterification reaction between a furan dicarboxylic acid compound and an aliphatic alcohol (A) having not less than 4 and not more than 22 carbon atoms (hereinafter also referred to as an "esterification reaction condensate"), in which the aliphatic alcohol (A) includes a saturated aliphatic alcohol (a1) and an unsaturated aliphatic alcohol (a2), and a content of the unsaturated aliphatic alcohol (a2) in the aliphatic alcohol (A) is not more than 25% by mass.

The plasticizer of the present invention has a plasticization performance for a halogen-based resin at a level identical to or higher than that of a phthalate-based plasticizer, and exhibits excellent effects of improving compatibility, heat resistance and cold resistance. The reason why the aforementioned excellent effects can be attained by the plasticizer of the present invention is considered as follow though it is not necessarily clearly determined.

In the plasticizer of the present invention, as the carboxylic acid component having π electrons, there is used the furan dicarboxylic acid compound having a furan ring whose molecular weight is smaller than that of a benzene ring. In consequence, it is considered that the esterification reaction condensate is likely to enter between polymer chains of the halogen-based resin, so that the plasticizer can be improved in compatibility with the halogen-based resin.

In addition, it is also considered that the esterification reaction condensate used in the present invention has a high crystallinity and therefore is hardly volatilized owing to strong interaction between molecules thereof which is caused by interaction between oxygen of the furan ring and the ester group, so that the obtained halogen-based resin composition can be improved in heat resistance.

Furthermore, it is considered that the esterification reaction condensate used in the present invention is allowed to enter between the polymer chains of the halogen-based resin to an appropriate extent and therefore can exhibit the effect of plasticizing the resin, so that the halogen-based resin becomes soft and is improved in cold resistance.

<Esterification Reaction Condensate>

The esterification reaction condensate used in the present invention is an intermolecular condensation product obtained by an esterification reaction between a furan dicarboxylic acid compound and an aliphatic alcohol (A) having 4 to 22 carbon atoms. The esterification reaction as used herein includes a direct reaction between a furan dicarboxylic acid or an acid anhydride thereof and an alcohol, and a reaction between a furan dicarboxylic acid ester and an alcohol.

Among these esterification reactions, from the viewpoint of good reactivity, etc., the direct reaction between a furan dicarboxylic acid or an acid anhydride thereof and an alcohol is preferred.

The aforementioned esterification reaction condensate is in the form of a mixture containing a furan dicarboxylic acid diester represented by the following general formula (1):

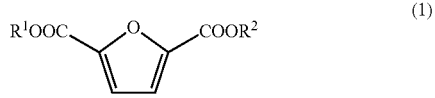

wherein $R^1$ and $R^2$ are each independently an aliphatic hydrocarbon group having not less than 4 and not more than 22 carbon atoms.

In the present invention, the aliphatic alcohol (A) having not less than 4 and not more than 22 carbon atoms as a raw material is used in the form of a mixture containing not more than 25% by mass of an unsaturated aliphatic alcohol (a2) and a saturated aliphatic alcohol (a1). Therefore, the esterification reaction condensate as the reaction product is in the form of a mixture containing (i) the diester of the general formula (1) in which the substituent groups $R^1$ and $R^2$ are both saturated aliphatic hydrocarbon groups; (ii) the diester of the general formula (1) in which one of the substituent groups $R^1$ and $R^2$ is a saturated aliphatic hydrocarbon group, and the other of the substituent groups $R^1$ and $R^2$ is an unsaturated aliphatic hydrocarbon group; and (iii) the diester of the general formula (1) in which the substituent groups $R^1$ and $R^2$ are both unsaturated aliphatic hydrocarbon groups.

$R^1$ and $R^2$ are respectively a hydrocarbon group derived from the aliphatic alcohol (A) having not less than 4 and not more than 22 carbon atoms as the raw material. The average number of carbon atoms in the hydrocarbon group is preferably not less than 6, more preferably not less than 7 and even more preferably not less than 9 from the viewpoint of improving heat resistance of the halogen-based resin composition in the case of compounding the obtained esterification reaction condensate therein, and is also preferably not more than 18, more preferably not more than 16, even more preferably not more than 13, further even more preferably not more than 12 and still further even more preferably not more than 11 from the viewpoint of improving cold resistance of the halogen-based resin composition as well as transparency and tensile properties of the resin.

<Furan Dicarboxylic Acid Compound>

The furan dicarboxylic acid compound used in the present invention includes a furan dicarboxylic acid represented by the following general formula (2), and an acid anhydride and an alkyl ester of the furan dicarboxylic acid.

As the furan dicarboxylic acid represented by the aforementioned general formula (2), from the viewpoint of improving heat resistance, cold resistance, compatibility and reactivity of the halogen-based resin composition containing the resulting esterification reaction condensate, preferred is 2,5-furan dicarboxylic acid or 3,4-furan dicarboxylic acid, and more preferred is 2,5-furan dicarboxylic acid.

<Aliphatic Alcohol (A) Having not Less than 4 and not More than 22 Carbon Atoms>

The aliphatic alcohol (A) having not less than 4 and not more than 22 carbon atoms (hereinafter also referred to merely as an "aliphatic alcohol (A)") is used in the form of a mixture containing a saturated aliphatic alcohol (a1) and an unsaturated aliphatic alcohol (a2) from the viewpoint of improving heat resistance, cold resistance and compatibility of the halogen-based resin composition containing the resulting esterification reaction condensate. The content of the unsaturated aliphatic alcohol (a2) in the aliphatic alcohol (A) is not more than 25% by mass.

The number of carbon atoms in the saturated aliphatic alcohol (a1) used in the aliphatic alcohol (A) is preferably not less than 4 and not more than 22, and the number of carbon atoms in the unsaturated aliphatic alcohol (a2) used in the aliphatic alcohol (A) is preferably not less than 14 and not more than 22.

From the viewpoint of improving heat resistance of the resulting halogen-based resin composition, the average number of carbon atoms in the aliphatic alcohol (A) is preferably not less than 6, more preferably not less than 7 and even more preferably not less than 9. Also, from the viewpoint of improving cold resistance of the resulting halogen-based resin composition as well as transparency and tensile properties of the resin, the average number of carbon atoms in the aliphatic alcohol (A) is preferably not more than 18, more preferably not more than 16, even more preferably not more than 13, further even more preferably not more than 12 and still further even more preferably not more than 11.

In this case, the average number of carbon atoms in the aliphatic alcohol (A) means a weighted mean value of the numbers of carbon atoms in the saturated aliphatic alcohol (a1) and the unsaturated aliphatic alcohol (a2) contained in the aliphatic alcohol (A).

(Saturated Aliphatic Alcohol (a1) Having not Less than 4 and not More than 22 Carbon Atoms)

The saturated aliphatic alcohol (a1) having not less than 4 and not more than 22 carbon atoms is preferably a saturated aliphatic alcohol (a1) having not less than 6 carbon atoms, and also preferably a saturated aliphatic alcohol (a1) having not more than 18 carbon atoms, more preferably not more than 16 carbon atoms, even more preferably not more than 14 carbon atoms and further even more preferably not more than 12 carbon atoms.

The saturated aliphatic alcohol (a1) is preferably in the form of a saturated aliphatic monovalent alcohol and more preferably a saturated linear aliphatic monovalent alcohol.

Specific examples of the saturated aliphatic alcohol (a1) having not less than 4 and not more than 22 carbon atoms include at least one alcohol selected from the group consisting of n-butanol, isobutanol, tert-butanol, n-pentanol, 2-methyl butanol, isopentanol, tert-pentanol, n-hexanol, 2-methyl pentanol, n-heptanol, 2-methyl hexanol, n-octanol, 2-methyl heptanol, 2-ethyl hexanol, n-nonanol, isononanol, n-decanol, isodecanol, n-undecanol, 3-ethyl-2-nonanol, n-dodecanol, n-tridecanol, isotridecanol, tetradecanol, pentadecanol, hexadecanol, octadecanol, eicosanol and docosanol, etc. Of these alcohols, preferred are n-hexanol, n-octanol, 2-ethyl hexanol, n-decanol and n-dodecanol.

(Unsaturated Aliphatic Alcohol (a2))

The unsaturated aliphatic alcohol (a2) used in the present invention is not particularly limited, and is preferably an unsaturated aliphatic alcohol having not less than 14 and not more than 22 carbon atoms, and more preferably an unsaturated aliphatic monovalent alcohol preferably having not less than 16 carbon atoms, and also preferably having not more than 20 carbon atoms and more preferably not more than 18 carbon atoms.

Specific examples of the unsaturated aliphatic alcohol having not less than 14 and not more than 22 carbon atoms include at least one alcohol selected from the group consisting of tetradecenyl alcohol, pentadecenyl alcohol, hexadecenyl alcohol, heptadecenyl alcohol, elaidyl alcohol, oleyl alcohol, nonadecenyl alcohol, erucyl alcohol, linoleyl alcohol, elaido-linoleyl alcohol and elaido-linolenyl alcohol, etc. Of these alcohols, preferred is oleyl alcohol.

The content of the unsaturated aliphatic alcohol (a2) in the aliphatic alcohol (A) is preferably not less than 1% by mass, more preferably not less than 2% by mass, even more preferably not less than 3% by mass, further even more preferably not less than 4% by mass and still further even more preferably not less than 6% by mass from the viewpoint of improving heat resistance of the resulting halogen-based resin composition as well as transparency of the resin, and is also not more than 25% by mass, preferably not more than 20% by mass, more preferably not more than 18% by mass, even more preferably not more than 15% by mass and further even more preferably not more than 13% by mass from the viewpoint of improving compatibility and cold resistance of the resulting halogen-based resin composition as well as transparency and tensile properties of the resin.

The content of the saturated aliphatic alcohol (a1) in the aliphatic alcohol (A) is not less than 75% by mass, preferably not less than 80% by mass, more preferably not less than 82% by mass, even more preferably not less than 85% by mass and further even more preferably not less than 87% by mass from the viewpoint of improving compatibility and cold resistance of the resulting halogen-based resin composition as well as transparency and tensile properties of the resin, and is also preferably not more than 99% by mass, more preferably not more than 98% by mass, even more preferably not more than 97% by mass, further even more preferably not more than 96% by mass and still further even more preferably not more than 94% by mass from the viewpoint of improving heat resistance of the resulting halogen-based resin composition.

In particular, the content of the saturated linear aliphatic monovalent alcohol in the aliphatic alcohol (A) is preferably not less than 60 mol %, more preferably not less than 70 mol % and even more preferably not less than 75 mol % from the viewpoint of improving heat resistance and cold resistance of the resulting halogen-based resin composition as well as transparency and tensile properties of the resin.

<Esterification Reaction Conditions>
(Amounts of Raw Materials Charged)

The amount of the aliphatic alcohol (A) charged at the time of initiation of the esterification reaction is preferably an excessive amount relative to a stoichiometric amount thereof. The stoichiometric amount of the aliphatic alcohol (A) used in the esterification reaction means a theoretical ratio thereof capable of producing the furan dicarboxylic acid diester represented by the general formula (1), and corresponds to a molar amount 2 times that of the furan dicarboxylic acid compound used.

That is, the amount of the aliphatic alcohol (A) charged is preferably not less than 2.0 mol, more preferably not less than 2.1 mol, even more preferably not less than 2.2 mol and further even more preferably not less than 2.3 mol on the basis of 1 mol of the furan dicarboxylic acid compound from the viewpoint of promoting and completing the esterification reaction, and is also preferably not more than 10 mol, more preferably not more than 4 mol and even more preferably not more than 3 mol on the basis of 1 mol of the furan dicarboxylic acid compound from the viewpoint of promoting the esterification reaction and removing an excessive amount of the alcohol remaining after completion of the reaction.

It is preferred that the content of water in the aliphatic alcohol used is reduced as small as possible. If a large amount of water is included in the aliphatic alcohol (A) as the raw material, there tends to occur such a risk that the water causes the toxicity to a below-mentioned catalyst (catalytic poison), and therefore the catalyst used in the reaction suffers from deterioration in catalytic activity.

(Catalyst)

As the catalyst used in the esterification reaction, there may be used any known esterification catalysts having good esterification capability. Of these esterification catalysts, preferred are organic metal catalysts.

Examples of the organic metal catalysts include at least one compound selected from the group consisting of organic tin compounds such as tin tetraethylate, butyl tin maleate, dimethyl tin oxide, monobutyl tin oxide, dibutyl tin oxide and dioctyl tin oxide; organic titanium compounds such as tetraisopropyl titanate, tetra-n-butyl titanate and tetra-2-ethylhexyl titanate; organic zinc compounds such as zinc acetate.

Of these organic metal catalysts, from the viewpoint of high reaction efficiency, etc., preferred are organic tin compounds, more preferred is at least one tin oxide compound selected from the group consisting of dimethyl tin oxide, monobutyl tin oxide, dibutyl tin oxide and dioctyl tin oxide, even more preferred is monobutyl tin oxide or dibutyl tin oxide, and further even more preferred is monobutyl tin oxide.

In addition, from the viewpoint of high productivity, preferred is at least one compound selected from the group consisting of tetraisopropyl titanate, tetra-n-butyl titanate and tetra-2-ethylhexyl titanate.

The amount of the catalyst used in the esterification reaction may vary depending upon the kind thereof, and is preferably not less than 0.01 part by mass, more preferably not less than 0.02 part by mass and even more preferably not less than 0.03 part by mass on the basis of 100 parts by mass of a total amount of the furan dicarboxylic acid compound and the aliphatic alcohol having not less than 4 and not more than 22 carbon atoms which are charged into a reactor from the viewpoint of sufficiently exhibiting a catalytic activity thereof, and is also preferably not more than 2 parts by mass, more preferably not more than 1 part by mass and even more preferably not more than 0.5 part by mass on the basis of 100 parts by mass of a total amount of the furan dicarboxylic acid compound and the aliphatic alcohol having not less than 4 and not more than 22 carbon atoms which are charged into a reactor from the viewpoint of high catalyst addition efficiency.

(Reaction Temperature, Reaction Pressure, etc.)

The esterification reaction may be conducted under reflux of the aliphatic alcohol (A) using a known reaction apparatus equipped with a facility capable of refluxing the aliphatic alcohol (A) as the raw material.

The reaction temperature may vary depending upon the kind of aliphatic alcohol (A) as the raw material, etc., and is preferably not lower than 60° C., more preferably not lower than 100° C. and even more preferably not lower than 150° C. from the viewpoint of high reactivity, and is also preferably not higher than 250° C., more preferably not higher than 230° C. and even more preferably not higher than 220° C. from the viewpoint of high yield of the esterification reaction product. When the reaction temperature is not lower than 60° C., the esterification reaction is allowed to proceed at a high reaction rate. When the reaction temperature is not higher than 250° C., it is possible to suppress production of undesirable reaction by-products.

The reaction pressure is usually not less than 13.3 kPa, and preferably not more than normal pressures. The reaction pressure can be controlled by a vapor pressure of the aliphatic alcohol used in the esterification reaction. More specifically, the reaction pressure may be controlled to a pressure at which the reaction mixture is kept in a boiled state, and furthermore it is preferred that the reaction pressure is controlled to a pressure at which water by-produced can be removed out of the system.

The reaction time may vary depending upon the kind of furan dicarboxylic acid compound and aliphatic alcohol (A) used in the esterification reaction, the reaction temperature, the amount of the catalyst used in the esterification reaction, etc., and is preferably not less than 1 hour and more preferably not less than 2 hours from the viewpoint of high reactivity. If the reaction time is sufficiently long, it is possible to reduce a load applied in the step of separating the unreacted dicarboxylic acid compound or a dicarboxylic acid monoester as a reaction intermediate product. On the other hand, from the viewpoint of high yield of the esterification reaction product, the reaction time is preferably not more than 24 hours and more preferably not more than 10 hours. If the reaction time is short, it is possible to suppress production of undesirable by-products and improve quality of the furan dicarboxylic acid diester produced.

(Additional Treatments)

In the esterification reaction, under the aforementioned reaction conditions, water produced in the reaction is removed out of the reaction system by azeotropic distillation with the aliphatic alcohol (A) to enhance the reaction rate near to 100%, and an excessive amount of the aliphatic alcohol (A) is separated from the reaction product. The resulting reaction mixture is then subjected to additional treatments by known methods such as alkali cleaning, water washing, adsorption of impurities, distillation, etc., to obtain a purified dicarboxylic acid diester.

The thus obtained dicarboxylic acid diester (esterification reaction condensate) may be used as a plasticizer that is to be incorporated into a halogen-based resin.

<Halogen-Based Resin>

The halogen-based resin used in the present invention means a homopolymer or a copolymer of a halogen-containing monomer, or a polymer that is modified with a halogen. Specific examples of the halogen-based resin include at least one resin selected from the group consisting of a vinyl chloride-based resin, polyvinylidene chloride, chlorinated polyethylene, chlorinated polypropylene, chloro-sulfonated polyethylene and a chloroprene rubber, etc.

(Vinyl Chloride-Based Resin)

Examples of the vinyl chloride-based resin include a vinyl chloride homopolymer as well as a copolymer of vinyl chloride with a monomer copolymerizable with the vinyl chloride (hereinafter also referred to as a "vinyl chloride copolymer"), a graft copolymer obtained by graft-copolymerizing vinyl chloride to a polymer other than the vinyl chloride copolymer, etc.

The aforementioned monomer copolymerizable with vinyl chloride may include those monomers having a reactive double bond in a molecule thereof. Examples of the monomer copolymerizable with vinyl chloride include α-olefins such as ethylene, propylene and butylene; vinyl esters such as vinyl acetate and vinyl propionate; vinyl ethers such as butyl vinyl ether and cetyl vinyl ether; unsaturated carboxylic acids such as acrylic acid and methacrylic acid; esters of acrylic acid or methacrylic acid such as methyl acrylate, ethyl methacrylate and phenyl methacrylate; aromatic vinyl compounds such as styrene and α-methyl styrene; halogenated vinyl compounds such as vinylidene chloride and vinyl fluoride; and N-substituted maleimides such as N-phenyl maleimide and N-cyclohexyl maleimide.

In addition, the polymer other than the vinyl chloride copolymer may include those polymers to which vinyl chloride can be graft-copolymerized. Examples of the polymer other than the vinyl chloride copolymer include an ethylene-vinyl acetate copolymer, an ethylene-vinyl acetate-carbon monoxide copolymer, an ethylene-ethyl acrylate copolymer, an ethylene-ethyl acrylate-carbon monoxide copolymer, an ethylene-methyl methacrylate copolymer, an ethylene-propylene copolymer, an acrylonitrile-butadiene copolymer and a polyurethane.

Of the aforementioned halogen-based resins, from the viewpoint of good flexibility, etc., preferred is at least one resin selected from the group consisting of vinyl chloride-based resins such as polyvinyl chloride, an ethylene-vinyl chloride copolymer, a vinyl acetate-vinyl chloride copolymer and a polyurethane-grafted polyvinyl chloride copolymer, polyvinylidene chloride and a chloroprene rubber, and more preferred is at least one resin selected from the group consisting of polyvinyl chloride, polyvinylidene chloride and a chloroprene rubber.

Furthermore, the aforementioned halogen-based resin may be used in the form of a polymer blend in combination with a non-halogen-based resin. Examples of the non-halogen-based resin include polyethylene, an ethylene-propylene rubber, an ethylene-vinyl acetate copolymer, an ethylene-ethyl acrylate copolymer, an ethylene-methyl methacrylate copolymer, an ethylene-methyl acrylate copolymer, a nitrile rubber, a polyester and a thermoplastic polyurethane.

[Halogen-Based Resin Composition]

The halogen-based resin composition of the present invention includes the plasticizer for a halogen-based resin according to the present invention.

The content of the plasticizer of the present invention in the halogen-based resin composition may be appropriately determined according to the applications of the halogen-based resin composition, and is preferably not less than 0.01 part by mass, more preferably not less than 0.1 part by mass, even more preferably not less than 1 part by mass and further even more preferably not less than 10 parts by mass, and is also preferably not more than 200 parts by mass, more preferably not more than 150 parts by mass, even more preferably not more than 125 parts by mass, further even more preferably not more than 110 parts by mass and still further even more preferably not more than 100 parts by mass, on the basis of 100 parts by mass of the halogen-based resin, from the viewpoint of improving heat resistance, cold resistance and plasticization effect of the resulting composition.

The halogen-based resin composition of the present invention may be further used in combination with other known ester compounds unless the advantageous effects of the present invention are adversely affected. In addition, the halogen-based resin composition of the present invention may be further compounded with various additives such as a stabilizer, a processing aid, a colorant, a filler, an antioxidant, an ultraviolet absorber, an antistatic agent, a lubricant, etc., if required.

Examples of the ester compounds that can be used in combination with the plasticizer of the present invention include esters of phthalic acid, adipic acid, trimellitic acid, phosphoric acid, etc.

Specific examples of the phthalic acid esters include dibutyl phthalate, di-2-ethylhexyl phthalate, diisononyl phthalate, diisodecyl phthalate and diundecyl phthalate. Specific examples of the adipic acid esters include di-2-ethylhexyl adipate, diisononyl adipate and diisodecyl adipate. Specific examples of the trimellitic acid esters include tri-2-ethylhexyl trimellitate and triisodecyl trimellitate. Specific examples of the phosphoric acid esters include tri-2-ethylhexyl phosphate and tricresyl phosphate.

The amount of the ester compound used is preferably within 5% by mass on the basis of a total mass of the plasticizer.

Examples of the stabilizer include metal soap compounds such as lithium stearate, magnesium stearate, magnesium laurate, calcium ricinolate, calcium stearate, barium laurate, barium ricinolate, barium stearate, zinc octylate, zinc laurate, zinc ricinolate and zinc stearate; organotin-based compounds such as dimethyl tin bis-2-ethylhexyl thioglycolate, dibutyl tin maleate, dibutyl tin bis(butyl maleate) and dibutyl tin laurate; and antimony mercaptide compounds. The amount of the stabilizer compounded in the halogen-based resin composition is from 0.1 to 20 parts by mass on the basis of 100 parts by mass of the halogen-based resin.

Examples of the processing aid include liquid paraffin, a polyethylene wax, stearic acid, stearamide, ethylene bis (stearamide), butyl stearate and calcium stearate. The amount of the processing aid compounded in the halogen-based resin composition is from 0.1 to 20 parts by mass on the basis of 100 parts by mass of the halogen-based resin.

Examples of the colorant include carbon black, lead sulfide, white carbon, titanium white, lithopone, red iron oxide, antimony sulfide, chrome yellow, chrome green, cobalt blue and molybdenum orange. The amount of the colorant compounded in the halogen-based resin composition is from 1 to 100 parts by mass on the basis of 100 parts by mass of the halogen-based resin.

Examples of the filler include calcium carbonate; metal oxides such as silica, alumina, clay, talc, diatomaceous earth and ferrite; and fibers or powders of glass, carbon and metals, glass beads, graphite, aluminum hydroxide, barium sulfate, magnesium oxide, magnesium carbonate, magnesium silicate and calcium silicate. The amount of the filler compounded in the halogen-based resin composition is from 1 to 100 parts by mass on the basis of 100 parts by mass of the halogen-based resin.

Examples of the antioxidant include phenol-based compounds such as 2,6-di-tert-butyl phenol, tetrakis[methylene-3-(3,5-tert-butyl-4-hydroxy phenol)propionate]methane and 2-hydroxy-4-methoxy benzophenone; sulfur-based compounds such as alkyl disulfides, thiodipropionic acid esters and benzothiazole; phosphoric acid-based compounds such as trisnonylphenyl phosphite, diphenyl isodecyl phosphite, triphenyl phosphite and tris(2,4-di-tert-butylphenyl)phosphite; and organometallic-based compounds such as zinc dialkyl dithiophosphates and zinc diaryl dithiophosphates. The amount of the antioxidant compounded in the halogen-based resin composition is from 0.2 to 20 parts by mass on the basis of 100 parts by mass of the halogen-based resin.

Examples of the ultraviolet absorber include salicylate-based compound such as phenyl salicylate and p-tert-butyl phenyl salicylate; benzophenone-based compounds such as 2-hydroxy-4-n-octoxy benzophenone and 2-hydroxy-4-n-methoxy benzophenone; benzotriazole-based compounds such as 5-methyl-1H-benzotriazole and 1-dioctyl aminomethyl benzotriazole; and cyanoacrylate-based compounds. The amount of the ultraviolet absorber compounded in the halogen-based resin composition is from 0.1 to 10 parts by mass on the basis of 100 parts by mass of the halogen-based resin.

Examples of the antistatic agent include anionic antistatic agents such as alkyl sulfonate-type antistatic agents, alkyl ether carboxylic acid-type antistatic agents and dialkyl sulfosuccinate-type antistatic agents; nonionic antistatic agents such as polyethylene glycol derivatives, sorbitan derivatives and diethanol amine derivatives; cationic antistatic agents such as quaternary ammonium salts, e.g., alkyl amide amine-type antistatic agents and alkyl dimethyl benzyl-type antistatic agents, and organic acid salts or hydrochloric acid salts, e.g., alkyl pyridinium-type antistatic agents; and amphoteric antistatic agents such as alkyl betaine-type antistatic agents and alkyl imidazoline-type antistatic agents. The amount of the antistatic agent compounded in the halogen-based resin composition is from 0.1 to 10 parts by mass on the basis of 100 parts by mass of the halogen-based resin.

Examples of the lubricant include silicones, liquid paraffin, a paraffin wax, fatty acids such as stearic acid and lauric acid and metal salts thereof, fatty acid amides, fatty acid waxes and higher fatty acid waxes. The amount of the lubricant compounded in the halogen-based resin composition is from 0.1 to 10 parts by mass on the basis of 100 parts by mass of the halogen-based resin.

The halogen-based resin composition of the present invention contains the plasticizer of the present invention in an amount of preferably not less than 0.01 part by mass, more preferably not less than 0.1 part by mass, even more preferably not less than 1 part by mass and further even more preferably not less than 10 parts by mass, and also in an amount of preferably not more than 200 parts by mass, more preferably not more than 150 parts by mass, even more preferably not more than 125 parts by mass, further even more preferably not more than 110 parts by mass and still further even more preferably not more than 100 parts by mass, on the basis of 100 parts by mass of the halogen-based resin. Furthermore, if required, various additives may be added to the halogen-based resin composition, and the resulting mixture may be mixed while stirring using a stirrer such as a mortar mixer, a Henschel mixer, a Banbury mixer and a ribbon blender to obtain a mixed powder of the halogen-based resin composition. In addition, the resulting mixture may be further melted and kneaded using a kneading apparatus such as a conical twin screw extruder, a parallel twin screw extruder, a single screw extruder, a co-kneader-type kneader and a roll kneader to obtain a pellet-shaped or paste-like material of the halogen-based resin composition.

The mixed powder or pellets of the halogen-based resin composition produced by the aforementioned method can be formed into a desired shape by known methods such as extrusion molding, injection molding, calender molding, press molding and blow molding. In addition, the paste-like material of the halogen-based resin composition can be formed into a desired shape by known methods such as spread molding, dipping molding, gravure molding and screen processing.

The thus obtained resin molded product is useful as pipes such as water pipes, building materials, packaging materials such as food packaging films, agricultural materials such as agricultural films, sheathing for electric wires, automobile interior materials, various leather products, various foamed products, general-purpose hoses, gaskets, packing, wall papers, floor materials, boots, toys, etc.

With respect to the aforementioned embodiments, the present invention further provides the following aspects relating to the plasticizer and the halogen-based resin composition containing the plasticizer.

<1> A plasticizer for a halogen-based resin including a condensate obtainable by an esterification reaction between a furan dicarboxylic acid compound and an aliphatic alcohol (A) having not less than 4 and not more than 22 carbon atoms, in which the aliphatic alcohol (A) includes a saturated aliphatic alcohol (a1) and an unsaturated aliphatic alcohol (a2), and a content of the unsaturated aliphatic alcohol (a2) in the aliphatic alcohol (A) is not more than 25% by mass.

<2> The plasticizer for a halogen-based resin according to the aspect <1>, wherein the aliphatic alcohol (A) includes the saturated aliphatic alcohol (a1) having not less than 4 and not more than 22 carbon atoms and the unsaturated aliphatic alcohol (a2) having not less than 14 and not more than 22 carbon atoms.

<3> The plasticizer for a halogen-based resin according to the aspect <1> or <2>, wherein an average number of carbon atoms in the aliphatic alcohol (A) is preferably not less than 6, more preferably not less than 7 and even more preferably not less than 9, and is also preferably not more than 18, more preferably not more than 16, even more preferably not more than 13, further even preferably not more than 12 and still further even preferably not more than 11.

<4> The plasticizer for a halogen-based resin according to any one of the aspects <1> to <3>, wherein the aliphatic alcohol (A) is preferably an aliphatic monovalent alcohol, and more preferably a linear aliphatic monovalent alcohol.

<5> The plasticizer for a halogen-based resin according to any one of the aspects <1> to <4>, wherein the aliphatic alcohol (A) preferably contains a linear aliphatic monovalent alcohol, in particular, a saturated linear aliphatic monovalent alcohol, in an amount of not less than 60 mol %, more preferably not less than 70 mol % and even more preferably not less than 75 mol %.

<6> The plasticizer for a halogen-based resin according to any one of the aspects <1> to <5>, wherein the saturated aliphatic alcohol (a1) is preferably a saturated aliphatic alcohol having not less than 6 carbon atoms, and also is preferably a saturated aliphatic alcohol having not more than 18 carbon atoms, more preferably not more than 16 carbon atoms, even more preferably not more than 14 carbon atoms and further even more preferably not more than 12 carbon atoms, and the saturated aliphatic alcohol (a1) is preferably in the form of a saturated aliphatic monovalent alcohol and more preferably a saturated linear aliphatic monovalent alcohol.

<7> The plasticizer for a halogen-based resin according to any one of the aspects <1> to <6>, wherein the saturated aliphatic alcohol (a1) is at least one alcohol selected from the group consisting of n-butanol, isobutanol, tert-butanol, n-pentanol, 2-methyl butanol, isopentanol, tert-pentanol, n-hexanol, 2-methyl pentanol, n-heptanol, 2-methyl hexanol, n-octanol, 2-methyl heptanol, 2-ethyl hexanol, n-nonanol, isononanol, n-decanol, isodecanol, n-undecanol, 3-ethyl-2-nonanol, n-dodecanol, n-tridecanol, isotridecanol, tetradecanol, pentadecanol, hexadecanol, octadecanol, eicosanol and docosanol.

<8> The plasticizer for a halogen-based resin according to any one of the aspects <1> to <7>, wherein the unsaturated aliphatic alcohol (a2) is an unsaturated aliphatic alcohol preferably having not less than 14 carbon atoms and more preferably not less than 16 carbon atoms, and also preferably having not more than 22 carbon atoms, more preferably not more than 20 carbon atoms and even more preferably not more than 18 carbon atoms.

<9> The plasticizer for a halogen-based resin according to any one of the aspects <1> to <8>, wherein the unsaturated aliphatic alcohol (a2) is at least one alcohol selected from the group consisting of tetradecenyl alcohol, pentadecenyl alcohol, hexadecenyl alcohol, heptadecenyl alcohol, elaidyl alcohol, oleyl alcohol, nonadecenyl alcohol, erucyl alcohol, linoleyl alcohol, elaido-linoleyl alcohol and elaido-linolenyl alcohol.

<10> The plasticizer for a halogen-based resin according to any one of the aspects <1> to <9>, wherein the unsaturated aliphatic alcohol (a2) is oleyl alcohol.

<11> The plasticizer for a halogen-based resin according to any one of the aspects <1> to <10>, wherein a content of the unsaturated aliphatic alcohol (a2) in the aliphatic alcohol (A)

is preferably not less than 1% by mass, more preferably not less than 2% by mass, even more preferably not less than 3% by mass, further even more preferably not less than 4% by mass and still further even more preferably not less than 6% by mass, and is also preferably not more than 20% by mass, more preferably not more than 18% by mass, even more preferably not more than 15% by mass and further even more preferably not more than 13% by mass.

<12> The plasticizer for a halogen-based resin according to any one of the aspects <1> to <11>, wherein an amount of the aliphatic alcohol (A) charged in the esterification reaction is preferably not less than 2.0 mol, more preferably not less than 2.1 mol, even more preferably not less than 2.2 mol and further even more preferably not less than 2.3 mol, and is also preferably not more than mol, more preferably not more than 4 mol and even more preferably not more than 3 mol, on the basis of 1 mol of the furan dicarboxylic acid compound.

<13> The plasticizer for a halogen-based resin according to any one of the aspects <1> to <12>, wherein a catalyst used in the esterification reaction is preferably an organic metal catalyst, more preferably at least one compound selected from the group consisting of an organic tin compound, an organic titanium compound and an organic zinc compound, and even more preferably at least one compound selected from the group consisting of dimethyl tin oxide, monobutyl tin oxide, dibutyl tin oxide, dioctyl tin oxide, tetraisopropyl titanate, tetra-n-butyl titanate and tetra-2-ethylhexyl titanate.

<14> The plasticizer for a halogen-based resin according to any one of the aspects <1> to <13>, wherein an amount of the catalyst used in the esterification reaction is preferably not less than 0.01 part by mass, more preferably not less than 0.02 part by mass and even more preferably not less than 0.03 part by mass, and is also preferably not more than 2 parts by mass, more preferably not more than 1 part by mass and even more preferably not more than 0.5 part by mass, on the basis of 100 parts by mass of a total amount of the furan dicarboxylic acid compound and the aliphatic alcohol having not less than 4 and not more than 22 carbon atoms which are charged into a reactor.

<15> The plasticizer for a halogen-based resin according to any one of the aspects <1> to <14>, wherein a reaction temperature used in the esterification reaction is preferably not lower than 60° C., more preferably not lower than 100° C. and even more preferably not lower than 150° C., and is also preferably not higher than 250° C., more preferably not higher than 230° C. and even more preferably not higher than 220° C.

<16> The plasticizer for a halogen-based resin according to any one of the aspects <1> to <15>, wherein the condensate is in the form of a mixture containing a furan dicarboxylic acid diester represented by the aforementioned general formula (1).

<17> The plasticizer for a halogen-based resin according to any one of the aspects <1> to <16>, wherein the halogen-based resin is preferably at least one resin selected from the group consisting of a vinyl chloride-based resin, polyvinylidene chloride, chlorinated polyethylene, chlorinated polypropylene, chloro-sulfonated polyethylene and a chloroprene rubber, and more preferably at least one resin selected from the group consisting of a vinyl chloride-based resin, polyvinylidene chloride and a chloroprene rubber.

<18> A halogen-based resin composition including the plasticizer according to any one of the aspects <1> to <17>.

<19> The halogen-based resin composition according to the aspect <18>, wherein a content of the plasticizer in the halogen-based resin composition is preferably not less than 0.01 part by mass, more preferably not less than 0.1 part by mass, even more preferably not less than 1 part by mass and further even more preferably not less than 10 parts by mass, and is also preferably not more than 200 parts by mass, more preferably not more than 150 parts by mass, even more preferably not more than 125 parts by mass, further even more preferably not more than 110 parts by mass and still further even more preferably not more than 100 parts by mass, on the basis of 100 parts by mass of the halogen-based resin.

<20> A process for producing a halogen-based resin composition, including the step of compounding the plasticizer according to any one of the aspects <1> to <17> with a halogen-based resin, an amount of the plasticizer compounded with the halogen-based resin being preferably not less than 0.01 part by mass, more preferably not less than 0.1 part by mass, even more preferably not less than 1 part by mass and further even more preferably not less than 10 parts by mass, and being also preferably not more than 200 parts by mass, more preferably not more than 150 parts by mass, even more preferably not more than 125 parts by mass, further even more preferably not more than 110 parts by mass and still further even more preferably not more than 100 parts by mass, on the basis of 100 parts by mass of the halogen-based resin.

EXAMPLES

In the following Examples and Comparative Examples, the respective properties were measured and evaluated by the following methods.

(1) Evaluation of Tensile Properties

A molded sheet of a halogen-based resin was punched into a #3 dumbbell shape to prepare a test specimen. The thus prepared test specimen was subjected to tensile test using a tensile tester "AUTOGRAPH AGS-X" available from Shimadzu Corporation to evaluate a stress at break of the test specimen by a breaking strength (MPa) thereof. The smaller the breaking strength value, the lower the tensile stress of the test specimen and the more excellent the plasticizability thereof.

In addition, an elongation of the test specimen was evaluated by a breaking elongation (%) thereof. The larger the breaking elongation value, the higher the elongation at break of the test specimen and the more excellent the plasticizability thereof.

(2) Evaluation of Compatibility (2-1) Evaluation of Transparency

According to JIS K 7105, a haze value of a 1 mm-thick resin-molded sheet was measured using a haze meter "HM-150" available from Murakami Color Research Laboratory Co., Ltd. The lower the haze value, the more excellent the transparency of the sheet and the more excellent the compatibility of the components in the sheet.

(2-2) Evaluation of Anti-Bleeding Properties

A non-molded sheet of a halogen-based resin was allowed to stand at 40° C. for 2 weeks. Then, the surface of the sheet was observed by naked eyes to evaluate an appearance of the sheet according to the following ratings. The less the occurrence of bleeding, the more excellent the compatibility of the components in the sheet.

○: No bleeding was recognized on a surface of the sheet.

×: Bleeding was recognized on a surface of the sheet.

(3) Evaluation of Heat Resistance

A test specimen formed of a halogen-based resin molded sheet punched into a #3 dumbbell shape was allowed to stand at 100° C. for 220 hours or for 430 hours in a Geer oven-type aging tester "AG-103" available from Ueshima Seisakusho Co., Ltd., as prescribed in JIS K 7212 to measure a rate of reduction of a weight thereof between before and after the standing test and thereby evaluate heat resistance of the test specimen. The lower the reduction rate, the more excellent the heat resistance of the test specimen.

(4) Evaluation of Cold Resistance

A Clash-Berg cold resistance test was conducted using "FLEXIBILITY TESTER" available from Toyo Seiki Seisaku-Sho, Ltd., by the method prescribed in JIS K 6745.

The obtained flexibility temperature Tf value was regarded and used as an index for evaluation of cold resistance of a test specimen formed of a halogen-based resin molded sheet. The lower the Tf value, the more excellent the cold resistance of the test specimen.

Production Example 1 (Production of Esterification Reaction Condensate E-1)

A 500 mL four-necked flask was charged with 100.0 g of 2,5-furan dicarboxylic acid available from V & V Pharma Industries, 99.0 g of n-octanol, 99.0 g of n-decanol, 25.0 g of n-dodecanol, 25.0 g of oleyl alcohol and 0.15 g of monobutyl tin oxide available from Tokyo Chemical Industry Co., Ltd., and the contents of the flask were mixed and heated, and maintained at 200° C. for 2 hours and 30 minutes to react the respective components with each other while distilling off water therefrom.

After completion of the reaction, the resulting reaction solution was cooled to 90° C., and then 0.2 g of 85% phosphoric acid, 1.5 g of non-crystalline synthetic magnesium silicate "KYOWARD 600S" available from Kyowa Chemical Industry Co., Ltd., 1.0 g of activated carbon "CARBOLAFIN" available from Japan EnviroChemicals, Ltd., and 1.0 g of activated clay "GALLEON EARTH" available from Mizusawa Industrial Chemicals, Ltd., were added thereto, followed by stirring the resulting mixture at 90° C. for 1 hour. Thereafter, the resulting mixture was heated to 200° C. at which the alcohols were distilled off therefrom under a reduced pressure of about 400 Pa (about 3 Torr). Then, the reaction pressure was returned to normal pressures, and the reaction mixture was cooled to 90° C. and subjected to suction filtration using a filter paper over which a filtering aid "RADIOLITE #700" available from Showa Chemical Industry Co., Ltd., was laid, thereby obtaining an esterification reaction condensate (furan dicarboxylic acid diester) E-1. The results are shown in Table 1.

Production Examples 2 to 13 (Production of Esterification Reaction Condensates E-2 to E-13)

The same procedure as in Production Example 1 was repeated except for using the aliphatic alcohol components and the furan dicarboxylic acid components shown in Table 1, thereby obtaining esterification reaction condensates E-2 to E-13. The results are shown in Table 1.

TABLE 1

| | | Esterification reaction condensates | | | | | | |
|---|---|---|---|---|---|---|---|---|
| | | E-1 | E-2 | E-3 | E-4 | E-5 | E-6 | E-7 |
| Aliphatic alcohol components | n-Hexanol | | | | | | | |
| | n-Octanol | 99.0 g (39.9) | 113.3 g (47.8) | | 199.0 g (90.0) | 186.0 g (80.0) | 132.7 g (60.0) | |
| | 2-Ethyl hexanol | | | | | | | 66.4 g (30.0) |
| | Isononanol | | | | | | | |
| | n-Decanol | 99.0 g (39.9) | 90.1 g (38.0) | | | | | |
| | n-Dodecanol | 25.0 g (10.1) | 22.3 g (9.4) | 223.2 g (90.0) | | | | |
| | Isotridecanol | | | | | | | |
| | Oleyl alcohol | 25.0 g (10.1) | 11.3 g (4.8) | 24.8 g (10.0) | 22.1 g (10.0) | 46.5 g (20.0) | 22.1 g (10.0) | 279.2 g (100) |
| Dicarboxylic acid components | 2,5-Furan dicarboxylic acid | 100.0 g | 100.0 g | 80.0 g | 100.0 g | 100.0 g | 100.0 g | 65.0 g |
| | Phthalic anhydride | | | | | | | |
| Average number of carbon atoms in aliphatic alcohol | | 9.6 | 9.2 | 11.5 | 8.5 | 9.1 | 8.5 | 18.0 |
| Content of unsaturated aliphatic alcohol in alcohol components (% by mass) | | 10.1 | 4.8 | 10.0 | 10.0 | 20.0 | 10.0 | 100 |

| | | Esterification reaction condensates | | | | | |
|---|---|---|---|---|---|---|---|
| | | E-8 | E-9 | E-10 | E-11 | E-12 | E-13 |
| Aliphatic alcohol components | n-Hexanol | | 248.7 g (87.8) | | | | |
| | n-Octanol | 146.0 g (70.0) | | 210.0 g (90.1) | 191.4 g (85.0) | | |
| | 2-Ethyl hexanol | 62.5 g (30.0) | | | | | |
| | Isononanol | | | | | 230.8 g (100) | |
| | n-Decanol | | | | 33.8 g (15.0) | | |
| | n-Dodecanol | | | | | | |

TABLE 1-continued

|  |  |  |  |  |  |  |
|---|---|---|---|---|---|---|
|  | Isotridecanol |  |  |  |  | 256.5 g (100) |
|  | Oleyl alcohol |  | 34.4 g (12.2) | 23.0 g (9.9) |  |  |
| Dicarboxylic acid components | 2,5-Furan dicarboxylic acid | 100.0 g | 80.0 g |  | 100.0 g | 80.0 g |
|  | Phthalic anhydride |  |  | 100.0 g | 100.0 g |  |
| Average number of carbon atoms in aliphatic alcohol |  | 8.0 | 6.6 | 8.5 | 8.3 | 9.0 | 13.0 |
| Content of unsaturated aliphatic alcohol in alcohol components (% by mass) |  | 0 | 12.2 | 9.9 | 0 | 0 | 0 |

Note
Numeral values in parentheses indicate % by mass based on a total amount of alcohol components Examples 1 to 10 and Comparative Examples 1 to 7

Using the respective esterification reaction condensates E-1 to E-13 obtained in Production Examples 1 to 13, a non-molded sheet and a molded sheet of a vinyl chloride resin were prepared by the following method, and the thus prepared sheets were evaluated with respect to heat resistance, cold resistance, transparency, tensile properties and anti-bleeding properties thereof. The results are shown in Table 2.

(1) Production of Vinyl Chloride Resin Non-Molded Sheet

One hundred parts by mass of a vinyl chloride resin "ZEST1400" (average polymerization degree: 1400) available from Shin Dai-Ichi Vinyl Corporation were mixed with 60 parts by mass in total of the esterification reaction condensate(s) shown in Table 2, 3 parts by mass of a Ca/Mg/Zn-based stabilizer for vinyl chloride resins "ADEKASTAB RUP-103" available from ADEKA Corporation and 0.5 part by mass of a lubricant "LUNAC S-70V" (stearic acid) available from Kao Corporation at room temperature. Thereafter, the resulting mixture was gelled at 170° C. using a 4-inch roll, and then kneaded for 10 minutes, thereby obtaining a resin non-molded sheet having such a composition as shown in Table 2.

(2) Production of Vinyl Chloride Resin Molded Sheet

The respective non-molded sheets were preheated at 170° C. for 3 minutes and then pressed for 2 minutes, thereby obtaining 1 mm-thick resin molded sheets.

TABLE 2

|  | Esterification reaction condensates | Aliphatic alcohol components (mol %) |  |  |  |  |  |  |  | Linear chain ratio (mol %) |
|---|---|---|---|---|---|---|---|---|---|---|
|  |  | nC6 | nC8 | 2EH | iC9 | nC10 | nC12 | iC13 | Ole |  |
| Example 1 | E-1 |  | 47.1 |  | 38.8 | 8.3 |  |  | 5.8 | 100 |
| Example 2 | E-2 |  | 54.3 |  | 35.6 | 7.5 |  |  | 2.6 | 100 |
| Example 3 | E-3 |  |  |  |  |  |  | 92.8 | 7.2 | 100 |
| Example 4 | E-4 |  | 94.9 |  |  |  |  |  | 5.1 | 100 |
| Example 5 | E-5 |  | 89.2 |  |  |  |  |  | 10.8 | 100 |
| Example 6 | E-6 |  | 63.2 | 31.6 |  |  |  |  | 5.1 | 68.3 |
| Example 7 | E-7/E-8*[1] |  | 65.6 | 28.1 |  |  |  |  | 6.3 | 71.9 |
| Example 8 | E-9 | 95.0 |  |  |  |  |  |  | 5.0 | 100 |
| Example 9 | E-7/E-8*[2] |  | 63.3 | 27.1 |  |  |  |  | 9.6 | 72.9 |
| Example 10 | E-7/E-8*[3] |  | 60.9 | 26.1 |  |  |  |  | 13.1 | 73.9 |
| Com. Ex. 1 | E-8 |  | 70.0 | 30.0 |  |  |  |  |  | 70 |
| Com. Ex. 2 | E-7 |  |  |  |  |  |  |  | 100 | 100 |
| Com. Ex. 3 | E-10 (phthalic acid) |  | 95.0 |  |  |  |  |  | 5.0 | 100 |
| Com. Ex. 4 | E-11 (phthalic acid) |  | 87.3 |  |  |  | 12.7 |  |  | 100 |
| Com. Ex. 5 | E-12 |  |  |  | 100 |  |  |  |  | 0 |
| Com. Ex. 6 | E-13 |  |  |  |  |  |  | 100 |  | 0 |
| Com. Ex. 7 | E-7/E-8*[4] |  | 59.9 | 25.7 |  |  |  |  | 14.5 | 74.3 |

|  | Average number of carbon atoms in aliphatic alcohol | Content of unsaturated aliphatic alcohol (%)*[5] | Tensile properties | |
|---|---|---|---|---|
|  |  |  | Breaking strength (MPa) | Elongation (%) |
| Example 1 | 9.7 | 10.1 | 215 | 360 |
| Example 2 | 9.3 | 4.8 | 212 | 360 |
| Example 3 | 12.4 | 10.0 | 225 | 340 |
| Example 4 | 8.5 | 10.0 | 210 | 370 |
| Example 5 | 9.1 | 20.0 | 215 | 355 |
| Example 6 | 8.5 | 10.0 | 230 | 345 |
| Example 7 | 8.6 | 12.1 | 220 | 340 |
| Example 8 | 6.6 | 12.2 | 205 | 385 |
| Example 9 | 9.0 | 17.9 | 230 | 330 |
| Example 10 | 9.3 | 23.7 | 245 | 315 |
| Com. Ex. 1 | 8.0 | 0 | 220 | 350 |

TABLE 2-continued

| | | | | |
|---|---|---|---|---|
| Com. Ex. 2 | 18.0 | 100 | — | — |
| Com. Ex. 3 | 8.5 | 9.9 | 225 | 335 |
| Com. Ex. 4 | 8.3 | 0 | 214 | 360 |
| Com. Ex. 5 | 9.0 | 0 | 220 | 340 |
| Com. Ex. 6 | 13.0 | 0 | 250 | 310 |
| Com. Ex. 7 | 9.5 | 25.9 | — | — |

| | Compatibility | | Heat resistance | | Cold resistance |
|---|---|---|---|---|---|
| | Transparency | Anti-Bleeding properties Observation by | | | |
| | Haze (%) | naked eyes | 220 Hr | 430 Hr | Tf (° C.) |
| Example 1 | 5.6 | ○ | 0.6 | 0.8 | −40.0 |
| Example 2 | 5.3 | ○ | 0.7 | 0.9 | −40.2 |
| Example 3 | 7.8 | ○ | 0.3 | 0.4 | −38.3 |
| Example 4 | 4.5 | ○ | 0.8 | 1.0 | −40.3 |
| Example 5 | 5.5 | ○ | 0.6 | 0.9 | −39.0 |
| Example 6 | 5.9 | ○ | 1.1 | 1.3 | −36.8 |
| Example 7 | 5.1 | ○ | 1.0 | 1.2 | −37.0 |
| Example 8 | 2.5 | ○ | 1.3 | 1.5 | −42.0 |
| Example 9 | 6.0 | ○ | 0.8 | 1.0 | −36.0 |
| Example 10 | 6.6 | ○ | 0.7 | 0.8 | −35.5 |
| Com. Ex. 1 | 10.0 | ○ | 1.3 | 1.8 | −37.0 |
| Com. Ex. 2 | — | — | — | — | — |
| Com. Ex. 3 | 12 | X | 0.8 | 0.9 | −37.5 |
| Com. Ex. 4 | 10.4 | ○ | 0.9 | 1.0 | −38.0 |
| Com. Ex. 5 | 12.7 | ○ | 1.5 | 1.8 | −31.0 |
| Com. Ex. 6 | 13.0 | ○ | 1.3 | 1.4 | −24.0 |
| Com. Ex. 7 | — | — | — | — | — |

Note
*[1]Mixture of E-7/E-8 = 10/90 (mass ratio)
*[2]Mixture of E-7/E-8 = 15/85 (mass ratio)
*[3]Mixture of E-7/E-8 = 20/80 (mass ratio)
*[4]Mixture of E-7/E-8 = 22/78 (mass ratio)
*[5]Content of unsaturated aliphatic alcohol in alcohol components (% by mass)

The details of abbreviations of the aliphatic alcohol components, etc., shown in Table 2 are as follows.

nC6: n-Hexanol "KALKOL 0698" available from Kao Corporation nC8: n-Octanol "KALKOL 0898" available from Kao Corporation 2E11: 2-Ethyl hexanol available from Wako Pure Chemical Industries, Ltd.

iC9: Isononanol (3,5,5-trimethyl-1-hexanol) available from Tokyo Chemical Industry Co., Ltd.

nC10: n-Decanol "KALKOL 1098" available from Kao Corporation nC12: n-Dodecanol "KALKOL 2098" available from Kao Corporation iC13: Isotridecanol mixture "TRIDECANOL" available from KH Neochem Co., Ltd.

Ole: Oleyl alcohol "RIKACOL 90B" available from New Japan Chemical Co., Ltd.

Phthalic acid: Phthalic anhydride available from KANTO CHEMICAL CO., INC.

From Table 2, it was recognized that the plasticizers obtained in Examples 1 to 10 exhibited sufficient plasticization performance (refer to tensile properties) when compounded in the halogen-based resin, and had excellent effects of improving compatibility (transparency and anti-bleeding properties), heat resistance and cold resistance as compared to the plasticizers obtained in Comparative Examples 1 to 7.

Meanwhile, in Comparative Examples 2 and 7, since the raw material mixtures were not gelled even when heated to 170° C., it was not possible to prepare a molded sheet, thereby failing to obtain evaluation results.

INDUSTRIAL APPLICABILITY

In accordance with the present invention, it is possible to provide a plasticizer for a halogen-based resin which has a plasticization performance for a halogen-based resin at a level identical to or higher than that of a phthalate-based plasticizer, and exhibits excellent effects of improving compatibility, heat resistance and cold resistance, and a halogen-based resin composition containing the plasticizer.

The invention claimed is:

1. A plasticizer for a halogen-based resin, the plasticizer comprising a mixture of furan dicarboxylic acid diester represented by the following general formula (1):

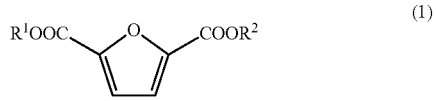

(1)

wherein $R^1$ and $R^2$ are each independently an aliphatic hydrocarbon group having not less than 4 and not more than 22 carbon atoms, wherein the mixture comprises the diester (i) wherein $R^1$ and $R^2$ are both saturated aliphatic hydrocarbon groups, the diester (ii) wherein one of $R^1$ and $R^2$ is a saturated aliphatic hydrocarbon group and the other of $R^1$ and $R^2$ is an unsaturated aliphatic hydrocarbon group, and the diester (iii) wherein $R^1$ and $R^2$ are both unsaturated aliphatic hydrocarbon groups, provided that a content of the unsaturated aliphatic hydrocarbon groups in $R^1$ and $R^2$ in the diester mixture is not more than 25% by mass in terms of monoalcohol.

2. The plasticizer for a halogen-based resin according to claim 1, wherein the halogen-based resin is at least one resin selected from the group consisting of a vinyl chloride-based resin, polyvinylidene chloride and a chloroprene rubber.

3. A halogen-based resin composition comprising the plasticizer according to claim 1.

4. The halogen-based resin composition according to claim 3, wherein a content of the plasticizer in the composition is not less than 0.01 part by mass and not more than 200 parts by mass on the basis of 100 parts by mass of the halogen-based resin.

5. A process for producing a halogen-based resin composition, comprising the step of compounding not less than 0.01 part by mass and not more than 200 parts by mass of the plasticizer according to claim 1 with 100 parts by mass of a halogen-based resin.

* * * * *